(12) United States Patent
Baughman et al.

(10) Patent No.: US 10,388,404 B2
(45) Date of Patent: Aug. 20, 2019

(54) USING MACHINE-LEARNING TO PERFORM LINEAR REGRESSION ON A DNA-COMPUTING PLATFORM

(71) Applicant: International Business Machines Corporation, Armonk, NY (US)

(72) Inventors: Aaron K. Baughman, Silver Spring, MD (US); Jennifer McDonough, Denver, CO (US); Sathya Santhar, Chennai (IN); Craig M. Trim, Sylmar, CA (US)

(73) Assignee: International Business Machines Corporation, Armonk, NY (US)

( * ) Notice: Subject to any disclaimer, the term of this patent is extended or adjusted under 35 U.S.C. 154(b) by 967 days.

(21) Appl. No.: 14/923,922

(22) Filed: Oct. 27, 2015

(65) Prior Publication Data

US 2017/0116372 A1   Apr. 27, 2017

(51) Int. Cl.
*G16B 40/00* (2019.01)
*G06N 20/00* (2019.01)
*G06N 3/12* (2006.01)

(52) U.S. Cl.
CPC ............ *G16B 40/00* (2019.02); *G06N 3/123* (2013.01); *G06N 20/00* (2019.01)

(58) Field of Classification Search
CPC .................................................... G16B 40/00
See application file for complete search history.

(56) References Cited

U.S. PATENT DOCUMENTS

| 6,876,930 | B2 | 4/2005 | Murray et al. |
| 6,950,753 | B1 | 9/2005 | Rzhetsky et al. |
| 7,167,847 | B2 * | 1/2007 | Sasagawa ............... B82Y 10/00 706/13 |
| 7,974,788 | B2 | 7/2011 | Rzhetsky et al. |
| 2002/0168664 | A1 | 11/2002 | Murray et al. |
| 2003/0224356 | A1 | 12/2003 | Knoll et al. |
| 2004/0143725 | A1 | 7/2004 | Addison |
| 2005/0064449 | A1 | 3/2005 | Knoll et al. |
| 2007/0094166 | A1 | 4/2007 | Addison |
| 2007/0161081 | A1 | 7/2007 | Jin et al. |
| 2007/0166788 | A1 | 7/2007 | Jin et al. |

(Continued)

OTHER PUBLICATIONS

Bel-Enguix et al., "A BioInspired Model for Parsing of Natural Languages", Studies in computational Intelligence (SCI) 129, 369-378, 2008. (Year: 2008).*

(Continued)

*Primary Examiner* — Paulinho E Smith

(74) *Attorney, Agent, or Firm* — Schmeiser, Olsen & Watts; Mark C. Vallone

(57) ABSTRACT

A method and associated systems for using machine-learning methods to perform linear regression on a DNA-computing platform. One or more processors generate and initialize beta coefficients of a system of linear equations. These initial values are encoded into nucleobase chains that are then padded to a standard length. The chains are allowed to bind with complementary template chains in a DNA-computing reaction, and the resulting DNA molecules are decoded to reveal the relative the relative likelihood of each chain to bind. The initial values of the beta coefficients are weighted proportionally to these likelihoods, and the process is repeated iteratively until the beta coefficients converge to optimal values.

20 Claims, 2 Drawing Sheets

(56) References Cited

U.S. PATENT DOCUMENTS

| | | | |
|---|---|---|---|
| 2009/0170769 A1 | 7/2009 | Jin et al. | |
| 2010/0146336 A1* | 6/2010 | Baughman | G06Q 10/04 714/26 |
| 2011/0314006 A1 | 12/2011 | Sweeny et al. | |
| 2012/0021486 A1 | 1/2012 | Dinu et al. | |
| 2012/0121591 A1 | 5/2012 | Sullivan et al. | |
| 2012/0156676 A1 | 6/2012 | Weidhaas et al. | |
| 2015/0149461 A1 | 5/2015 | Aguilar Lemarroy et al. | |
| 2015/0379399 A1* | 12/2015 | Baughman | G06F 17/274 706/13 |
| 2017/0116372 A1* | 4/2017 | Baughman | G06N 3/123 |
| 2017/0342478 A1* | 11/2017 | Jawaharlal | C12Q 1/6869 |
| 2019/0095585 A1* | 3/2019 | Jawaharlal | G16H 15/00 |

OTHER PUBLICATIONS

Office Action (dated Jan. 13, 2017) for U.S. Appl. No. 14/318,852, filed Jun. 30, 2014.
Amendment (dated Jan. 18, 2017) for U.S. Appl. No. 14/318,852, filed Jun. 30, 2014.
Bei-Enguix et al, "A BioInspired Model for Parsing of Natural Languages", Studies in Computational Intelligence (SCI) 129, 369-378 (2008), Springer-Verlag Berlin Heidelberg 2008.
Ferretti et al, "Remarks on Relativisations and DNA Encodings", Molecular Computing (Head Festschrift), LNCS 2950, pp. 132-138, 2004, Springer-Verlag Berlin Heidelberg 2004.
List of IBM Patents or Patent Applications Treated as Related; attached Oct. 27, 2015; 1 page.
Xavier Liora et al., Towards Better than Human Capability in Diagnosing Prostate Cancer Using Infrared Spectroscopic Imaging, GECCO '07, Jul. 7-11, 2007, ACM 978-1-59593-697-4/07/0007, 8 pages.
Blas, et al., The UCSC Kestrel Parallel Processor, IEEE Transactions on Parallel and Distributed Systems, vol. 16, No. 1, Jan. 2005, pp. 80-92.
Gao et al., A Structure-based Approach to Predicting in vitro Transcription Factor-DNA Interaction, 2013, 978-1-4799-3462-1/13, 1 page.
Arun et al., Large-scale testing of chemical prediction algorithms and improved machine learning-based approaches to shift prediction, Aug. 2004, Proceedings of the 2004 IEEE Computational Systems Bioinformatics Conference, 2 page.
Park et al., Image-based Automated Chemical Database Annotation with Ensemble of Machine-Vision Classifiers, 6th Annual IEEE Conference on Automation Science and Engineering, Canada, Aug. 21-24, 2010, pp. 168-173.
De Meo et al., HT-RLS: High-Throughput web tool for analysis of DNA microarray data using RLS classifiers, Eighth IEEE International Symposium on Cluster Computing and the Grid, 978-0-7695-3156-4/08, 2008 DOI 10.1109/CCGRID.2008.108, pp. 747-752.
Ha et al., Evolutionary Hypernetwork Models for Aptamer-Based Cardiovascular Disease Diagnosis, GECCO'07, Jul. 7-11, 2007, London, England, ACM 978-1-59593-698-1/07/0007, pp. 2709-2716.
Ray et al., RNA Secondary Structure Prediction Using Soft Computing, IEEE/ACM Transactions on Computational Biology and Bioinformatics, vol. 10, No. 1, Jan./Feb. 2013, pp. 2-17.
Ashlock et al., Distinguishing Endogenous Retroviral LTRs from SINE Elements Using Features Extracted from Evolved Side Effect Machines, IEEE/ACM Transactions on Computational Biology and Bioinformatics, vol. 9, No. 6, Nov./Dec. 2012, pp. 1676-1689.
Jiao et al., Artificial DNA Computing-Based Spectral Encoding and Matching Algorithm for Hyperspectral Remote Sensing Data, IEEE Transactions on Geoscience and Remote Sensing, vol. 50, No. 10. Oct. 2012, pp. 4085-4104.
Zhang et al., DNA-Based Fixed Gain Amplifiers and Linear Classifier Circuits, Y. Sakakibara and Y. Mi (Eds.): DNA 16, LNCS 6518, pp. 176-186, 2011, copyright Springer-Verlag Berlin Heidelberg, 2011.
Scott K. Silverman, DNA as a Versatile Chemical Component for Catalysis Encoding, and Stereocontrol, DOI: 10.1002/anie. 200906345, www.angewandt.org, 2010 Wiley-VCH Verlag GmbH & Co. KGaA, Weinheim, Angew. Chem. Int. Ed. 2010, 49, pp. 7180-7201.

* cited by examiner

USING MACHINE-LEARNING TO PERFORM LINEAR REGRESSION ON A DNA-COMPUTING PLATFORM

TECHNICAL FIELD

The present invention relates to performing a linear regression analysis by implementing a machine-learning algorithm on a DNA-computing platform.

BACKGROUND

A DNA computer uses chemical reactions to perform computational tasks by taking advantage of the fact that information may be stored in DNA molecules and in the chains of nucleobases (generally referred to here as "bases") that comprise DNA molecules. An element of data may thus be encoded into a molecular chain of bases, much like the way in which a sequence of binary digits stored in conventional computer memory might represent a numeric value or a string of text.

Computational operations may be performed on such encoded data because certain types of bases more readily pair (or chemically bind) with each other to form "base pairs" through a process known in the art as Watson-Crick bonding. It is therefore possible to organize bases into a pair of complementary sequences that combine into a double-helix DNA molecule when mixed together in an appropriate medium. The resulting DNA molecule may then represent a result of a logical or arithmetic operation performed upon data elements represented by the two sequences.

If, for example, a first base A1 binds to a second (complementary) base A2 and a third base B1 binds to its complementary, fourth base B2, the first four bases of a molecular sequence A1-B1-B1-B1-B2 will bind with the last four bases of a second molecule comprising the sequence A1-A1-A1-A2-B2-B2-B2 when the two are mixed together and allowed to react. The resulting DNA molecule, in which the two initial molecular sequences are bound together in a double-helix structure, may, through proper encoding, thus represent a relationship between the two sequences or a result of an operation performed upon the two sequences.

In this way, a pair of complementary sequences may be used to implement data-processing functions like an arithmetic or logical operation, a pattern-matching function, a database lookup, or a sorting operation. In a syntactical-analysis application, for example, two sequences might be configured to pair only if both those sequences represent data elements that satisfy a common set of criteria, such as identifying a part of speech. Similarly, in a data-analysis application, two sequences might be configured to bind together only if the two represent information stored in a same data-storage format, such as a numeric integer format.

In an example that continues to use the above sequence-naming convention, a first molecule, comprising a first sequence A1-A1-A1-A2-B2-B2-B2, could be used to identify data values stored as integer variables if the first sequence is configured to bind only with sequences that represent integer data values. A second sequence into which has been encoded an integer number might further comprise a complementary subsequence A1-B1-B1-B1. When mixed together in an appropriate medium, the last four nucleobases of the first molecule (A2-B2-B2-B2) would bind with the second molecule's A1-B1-B1-B1 subsequence. The resulting DNA molecule could then be decoded or interpreted to specify that information represented by one strand of the resulting double-helix may be identified as an integer value by information encoded into the second strand.

In this way, data structures and complex data-processing operations may be encoded into molecular "programs" and such a program may be "run" by allowing carefully sequenced chains of nucleobases selectively bind together in a chemical reaction.

One advantage of DNA computing is that it allows an enormous number of information-bearing molecules to be mixed together in just a drop of medium, where they may combine almost instantaneously, consuming a tiny fraction of the energy required by by electronic computers. When used to solve certain types of highly parallel, data-intensive operations, they can produce results far more quickly and efficiently than even the most powerful conventional computer systems.

Machine learning is a field of computer science in which a computer program continuously revises itself in response to patterns it detects in its input data. Rather than following an unchanging, predetermined, set of instructions, a machine-learning program automatically updates a data model as a function of its input, and bases inferences, decisions, computations, and output at least partially upon updated characteristics of that data model.

Machine-learning applications are useful in fields where a system must adapt to highly dynamic or difficult-to-quantize data, such as computational statistics, optical-character recognition, search, optimization, malware prevention, spam filtering, voice-recognition, speech-recognition, and Web analytics. In such applications, a machine-learning application trains itself by identifying and correlating characteristics or patterns of each new input it receives, using the resulting inferences to make its output more accurate or efficient.

When implemented on a conventional computing platform, the high degree of parallelism, recursion, or computational complexity required by many machine-learning applications can impose a great burden on a conventional electronic, scalar, computer system. However, implementing machine-learning algorithms and models on a massively parallel, energy-efficient DNA-computing platform would extend the benefits of machine-learning applications into areas where it would not otherwise be cost-effective or computationally practical. No such solution exists today.

BRIEF SUMMARY

A first embodiment of the present invention provides a method for using machine-learning on a DNA-computing platform to perform linear regression, the method comprising:

a processor of a computer system identifying a first set of equal-length nucleobase sequences, wherein the identifying each sequence comprises selecting an order of nucleobases that each encode two or more numeric values of a set of numeric values, and wherein each value encoded into a first sequence of the first set of sequences represents an estimated value of a beta coefficient comprised by a corresponding first equation of a system of linear equations;

the processor further identifying a second set of equal-length nucleobase sequences that are each capable of bonding through a Watson Crick reaction to a corresponding sequence of the first set of equal-length nucleobase sequences;

the processor adjusting each value of the set of numeric values as a function of a result of a Watson Crick reaction between a first set of nucleobase chains and a second set of nucleobase chains, wherein each chain of the first set of nucleobase chains comprises nucleobases ordered in a sequence of the first set of nucleobase sequences, and wherein each chain of the second set of nucleobase chains comprises nucleobases ordered in a sequence of the second set of nucleobase sequences;

the processor replacing each value of the set of numeric values with its corresponding adjusted value; and the processor repeating the identifying, further identifying, adjusting, and replacing until the adjusted values converge over two or more successive adjustings to a constant set of values.

A second embodiment of the present invention provides a computer program product, comprising a computer-readable hardware storage device having a computer-readable program code stored therein, said program code configured to be executed by a processor of a computer system to implement a method for using machine-learning on a DNA-computing platform to perform linear regression, the method comprising:

the processor identifying a first set of equal-length nucleobase sequences, wherein the identifying each sequence comprises selecting an order of nucleobases that each encode two or more numeric values of a set of numeric values, and wherein each value encoded into a first sequence of the first set of sequences represents an estimated value of a beta coefficient comprised by a corresponding first equation of a system of linear equations;

the processor further identifying a second set of equal-length nucleobase sequences that are each capable of bonding through a Watson Crick reaction to a corresponding sequence of the first set of equal-length nucleobase sequences;

the processor adjusting each value of the set of numeric values as a function of a result of a Watson Crick reaction between a first set of nucleobase chains and a second set of nucleobase chains, wherein each chain of the first set of nucleobase chains comprises nucleobases ordered in a sequence of the first set of nucleobase sequences, and wherein each chain of the second set of nucleobase chains comprises nucleobases ordered in a sequence of the second set of nucleobase sequences;

the processor replacing each value of the set of numeric values with its corresponding adjusted value; and the processor repeating the identifying, further identifying, adjusting, and replacing until the adjusted values converge over two or more successive adjustings to a constant set of values.

A third embodiment of the present invention provides a computer system comprising a processor, a memory coupled to said processor, and a computer-readable hardware storage device coupled to said processor, said storage device containing program code configured to be run by said processor via the memory to implement a method for using machine-learning on a DNA-computing platform to perform linear regression, the method comprising:

the processor identifying a first set of equal-length nucleobase sequences, wherein the identifying each sequence comprises selecting an order of nucleobases that each encode two or more numeric values of a set of numeric values, and wherein each value encoded into a first sequence of the first set of sequences represents an estimated value of a beta coefficient comprised by a corresponding first equation of a system of linear equations;

the processor further identifying a second set of equal-length nucleobase sequences that are each capable of bonding through a Watson Crick reaction to a corresponding sequence of the first set of equal-length nucleobase sequences;

the processor adjusting each value of the set of numeric values as a function of a result of a Watson Crick reaction between a first set of nucleobase chains and a second set of nucleobase chains, wherein each chain of the first set of nucleobase chains comprises nucleobases ordered in a sequence of the first set of nucleobase sequences, and wherein each chain of the second set of nucleobase chains comprises nucleobases ordered in a sequence of the second set of nucleobase sequences;

the processor replacing each value of the set of numeric values with its corresponding adjusted value; and the processor repeating the identifying, further identifying, adjusting, and replacing until the adjusted values converge over two or more successive adjustings to a constant set of values.

DETAILED DESCRIPTION

Figure 1:
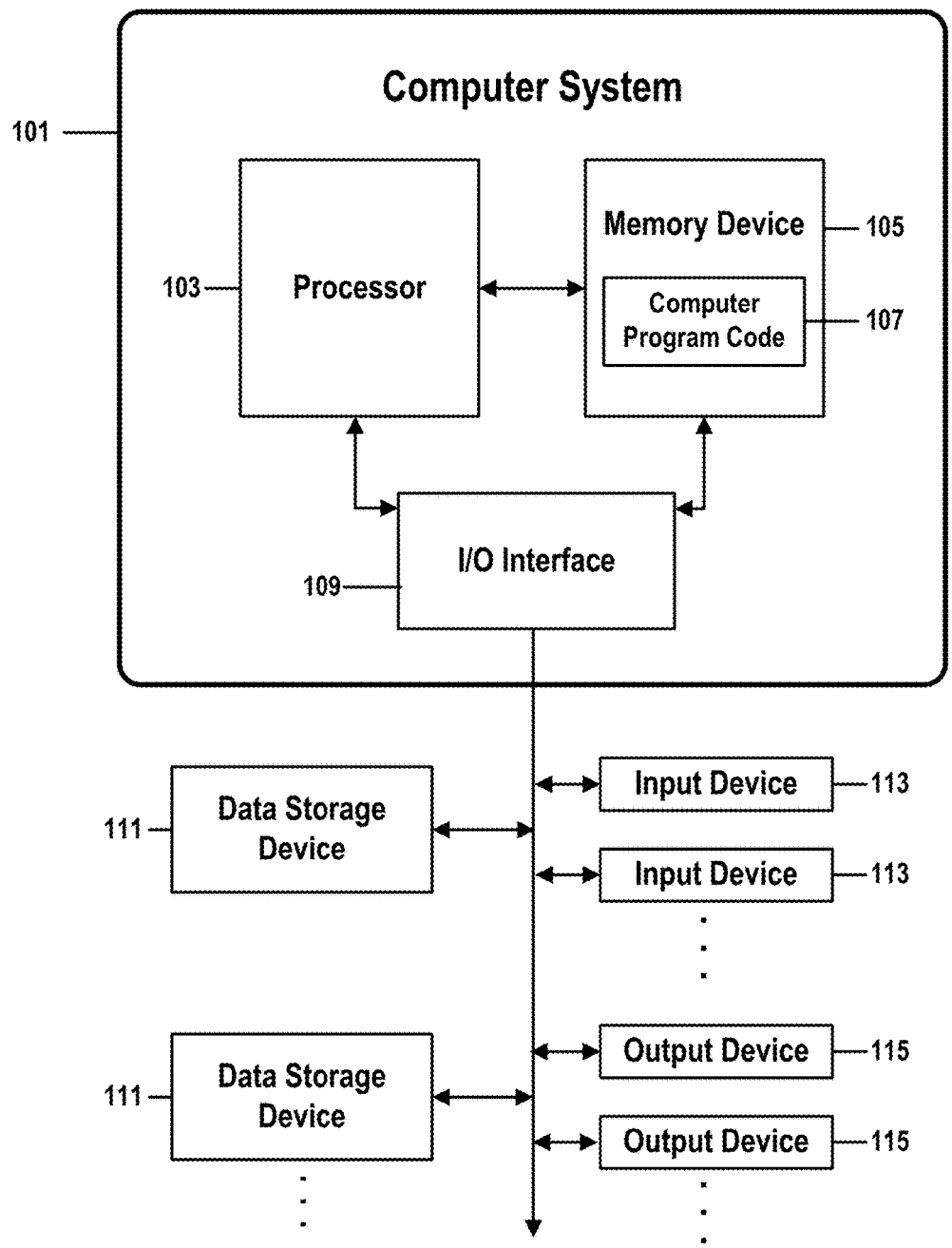
FIG. 1 shows the structure of a computer system and computer program code that may be used to implement a method for using machine-learning methods to perform linear regression on a DNA-computing platform.

Systems and methods of the present invention enhance current methods of DNA computing by manipulating the reaction rate of a chemical reaction by which a DNA-computing operation is performed. This manipulating may be performed by adjusting one or more physical characteristics of the input molecules or of the medium in which the reaction takes place, such as a temperature, a concentration, a static or dynamic gas or liquid pressure, a molecular bonding strength, a strength or concentration of a catalyst, or a molecular surface area.

Such embodiments may use such manipulation to identify a value of a coefficient (such as an array of "beta" regression coefficients of a linear-regression analysis), of a set of neural network weightings used to bias squashing functions, or of any other type of mathematical constant, coefficient, or variable that may bias, scale, or otherwise affect an overall data distribution of a solution to a DNA-computing problem.

Embodiments of the present invention implement such enhancements through a novel technique of encoding data into nucleobase chains of different lengths (that is, where each chain may comprise a different number of nucleobases). Because changing a reaction rate of a DNA-computing operation alters the relative rates at which chains of different lengths bind into DNA molecules, the distribution of molecules resulting from such a reaction may be optimized by manipulating physical characteristics of the reaction to set the reaction rate to an optimal rate. As will be explained below, this optimal distribution may then be interpreted as an identification of one or more optimized coefficients of an equation or other computational entity represented by the DNA operation.

A DNA molecule is a molecule of deoxyribonucleic acid, a lengthy linear polymer found in nature within a nucleus of a cell. A DNA molecule comprises two chains of molecules known as nucleobases (or "bases"), entwined around each other into a double helix. These chains each comprise a sequence of four types of nucleobases and the order of nucleobases in such a sequence may be used to encode information, much like the way that an order of a sequence of 1's and 0's in a byte of computer memory may encode information.

DNA computing is a form of computing that, rather than using traditional silicon-based computer technologies, encodes and stores data in a sequenced chain of nucleobases and processes that data by allowing such chains to bind together into DNA molecules. The resulting data manipulation represented by the binding may be analogous to functions performed by electronic components, such as flip-flops or a digital-logic gate. By decoding information represented by the resulting DNA molecules, it is possible to identify a result of a computation, wherein the input to the computation was represented by the initial nucleobase sequences and the performance of the computation is represented by the chemical reaction and its results.

A DNA "computer" can, for example, perform logical AND, OR, or NOT operations upon a pair of data elements that are each represented by a chain of nucleobases. The performance of such an operation may be performed by allowing the two chains to chemically react in certain ways. Such chemical reactions, known to those skilled in the art of molecular biology, DNA computing, and related fields, may be triggered by mixing together, or otherwise combining, one or more instances of each data-representing chain, possibly in the presence of a triggering enzyme.

If input data has been encoded into the nucleobase chains prior to initiating a DNA-computing operation that comprises a chemical reaction between the chains, the resulting DNA molecules may be decoded or analyzed to reveal output data that would have been produced by subjecting the input data to a computation that is analogous to the results of the reaction. Specifically, the pattern, position, or organization of bonds between the chains of a resultant DNA molecule may be decoded to yield information, and the arrangement and position of the chains in the resultant DNA molecule may be decoded to yield information.

Each nucleobase in this context may be any one of four types of molecules, each of which is commonly identified in the literature (although not in the naming-convention generally used in this document) by a single-letter abbreviation: adenine (A), cytosine (C), guanine (G), and thymine (T).

A sequence of these molecules may be linked in a chain represented here as a sequential listing of the nucleobases in the chain. As described above, an order of nucleobases in such a sequence may be deemed to represent information, much as an order of 1's and 0's in a byte of binary computer data may be deemed to represent an eight-bit number.

In one example, a first nucleobase sequence A1-A2-B1 (for example, A-T-C or G-C-A) can be deemed to represent a TRUE state of a logical variable and a second nucleobase sequence A1-A2-A1 (for example, C-G-C or T-A-T) might be deemed to represent a FALSE condition of the variable. Because nucleobase chains may comprise very long sequences, this mechanism allows an enormous amount of information to be represented by a single molecule.

In this document, we will refer to a process of translating information into an equivalent sequence of nucleobases as "encoding" the data. Similarly, we will refer to a process of identifying a piece of data that has been encoded into a sequence of nucleobases as a step of "decoding" the data.

The manner in which an input data element is associated with a particular nucleobase sequence may be implementation-dependent, based upon expert knowledge of the input data source or of a physical or chemical characteristic of the embodiment, or upon other techniques, knowledge, or tools known to one skilled in the art of information-processing, DNA computing, molecular biology, natural-language processing, or a related art.

In a typical DNA-computing operation, a set of nucleobase chains are each encoded with input data. This encoding may comprise using methods, technologies, or techniques known in the art to generate strands or chains of nucleobases in which nucleobases are ordered into specific sequences that represent the input data. In some cases, many copies of each molecular sequence may be created in this manner.

These molecules are then combined by methods known to those skilled in the art. They may, for example, be simply mixed together in a vessel. Such mixing may be facilitated by the addition of enzymes, other catalysts, or other chemical components that enable or facilitate a desired chemical reaction. This mixing process may happen quickly, often in a fraction of a second, and requires far less energy than that required by a conventional electronic computer. Because this mixing procedure may simultaneously combine large numbers of molecules, it may be used to quickly perform massively parallel operations.

If the combination is successful, some of the input molecules may stick together, break apart, or recombine to form new sequences of nucleobases. The order of nucleobases in these new sequences may be decoded by inverting the previous encoding procedure in order to reveal output data. This output data is analogous to output data that would be produced by applying a computational operation upon the input data, wherein the computational operation is analogous to the operation of the chemical reaction comprised by the mixing.

Embodiments of the present invention comprise steps that employ known methods, similar to those described above, to perform computational procedures by means of biochemical interactions among DNA molecules.

Embodiments of the present invention described in this document comprise methods and systems for implementing machine-learning applications on a DNA-computing platform. These methods may enhance such implementations with novel techniques of configuring physical properties of a DNA-computing chemical reaction in order to control a reaction rate of the reaction. In such embodiments, the reaction rate may be used to represent extrinsic weightings, constants, coefficients, and other parameters of a computational algorithm encoded into the molecules, thus allowing such coefficients to be optimized by configuring the physical properties.

These physical properties may comprise, but are not limited to, combinations of static or hydrostatic liquid pressure, temperature, an introduction of one or more catalysts, a catalyst strength, a molecular density or solution concentration, a gas pressure or volume, and a molecular bonding strength. This document will refer to these properties generically as "kinetics," but this pedagogical shortcut should not be construed to limit such properties to those that are related to a kinetic energy of a chemical reaction Similarly, the examples cited in this document should not be construed to limit the scope of the present invention to machine-learning algorithms, to DNA-computing platforms, or to using physical properties of chemical reactions solely to represent or optimize weightings, constants, and coefficients of mathematical equations.

The present invention's method of adjusting physical properties of reagents, chemical reactions, media, or molecules may be extended beyond the field of DNA computing to other embodiments in which information may be encoded into molecules, nanoparticles, atoms, subatomic particles, or other types of structures, such as chains of organic molecules, polysaccharides, nanostructures, or polyesters.

Nonetheless, all such embodiments comprise a concept of encoding algorithmic logic and data values into microscopic or nanoscopic structures, allowing those structures to interact in order to perform a logical, arithmetic, or computational operation upon the encoded logic or data, decoding the results of the interaction, and optimizing an overarching parameter of the interaction by encoding values of that parameter into a setting, configuration, or value of a physical characteristic of an entity associated with the interaction.

In DNA-computing embodiments described in this document, sequences of amino acids or nucleobases must be carefully ordered both to represent a desired data value, data structure, or data type, and also to include a subsequence of nucleobases that are complementary to, and that will bind to, an other sequence that represents a related data value, structure, or type.

Because this invention comprises ways to manipulate logical entities and software structures encoded into microscopic structures or in a chemical medium, the remainder of this document will continue to use the aforementioned convention of representing nucleobases logically, rather than forcing examples to reference specific sequences of the molecules adenine, cytosine, guanine, and thymine.

Even if limited to the scope of DNA-computing embodiments, a goal of the examples presented here is to describe how complementary molecules, nucleobases, or other information-carrying entities may bind together, not whether a chain of such entities contains a specific sequence of A, C, D, and T nucleobases.

Those skilled in a field related to molecular computing understand that in real-world DNA computing, within the context of the present invention, an adenine nucleobase and a thymine nucleobase may be considered "complementary" because of their affinity to bind to each other to form an A-T base pair. Similarly, a cytosine nucleobase and a guanine nucleobase might also be considered "complementary" because of their affinity to bind to each other to form a C-G base pair.

Within the context of the present invention, a specific sequence of nucleobases in a first chain is not as important as whether each nucleobase of the chain is complementary to, and will thus bind to, a corresponding nucleobase of a second chain. Furthermore, in embodiments not described in detail in this document, a method of encoding data into chains of complementary molecules may not even involve DNA molecules or nucleobases. Thus, the convention used in examples here, rather than identifying specific nucleobases, will merely specify entities that are each complementary to, and have an affinity to bind to or pair with, a matching entity.

In the convention used herein, therefore, nucleobase (or other molecule) A1 is deemed to be complementary to nucleobase (or other molecule) A2 and, similarly, B1 is deemed to be complementary to B2. On a DNA-computing platform, therefore, a first nucleobase sequence that contains a subsequence A1-A1-B2 would bind to a second nucleobase sequence that contains a subsequence A2-A2-B1.

This nomenclature does not identify specific nucleobases. A1 and A2 may comprise any first complementary pair of nucleobases, and B1 and B2 may respectively represent either of the other two nucleobases. If, for example, A1 identifies nucleobase cytosine, A2 will identify cytosine's complementary base, guanine, and B1 and B2 will respectively identify either adenine and thymine or thymine and adenine. Conversely, if B1 is interpreted to represent guanine, B2 would represent cytosine, and A1 and A2 would represent, respectively, either adenine and thymine or thymine and adenine.

Nucleobase sequences may be encoded to have different lengths, or they may be encoded to be a same length, regardless of whether they comprise information-bearing subsequences of different lengths.

If, for example, a first sequence of nucleobases represents a first element of data as a three-base sequence A1-A2-B1 and a second sequences encodes a second data element as a two-base sequence B2-A1, those two logical elements may be represented respectively as a three-base sequence and as a two-base sequence.

However, in some embodiments, these two elements may be represented by a pair of same-length sequences, in which extra positions are occupied by an arbitrary filler base. In one example, in which nucleobase B2 is deemed to be a filler, and in which it is determined that all sequences should have a length of five, the two logical elements might be respectively represented as: A1-A2-B1-B2-B2 and B2-A1-B2-B2-B2.

In such cases, each sequence in the embodiment would have to be carefully encoded to avoid accidentally binding to a filler string. This might be accomplished, for example, by an encoding strategy that avoids encoding data elements as strings of repeated B1 positions.

The length of an encoded sequence can be important because a likelihood that two sequences will bind may be a function of the lengths of those sequences. Furthermore, this likelihood can be adjusted by altering a reaction rate of a chemical reaction in which a DNA-computing operation takes place. As the reaction rate increases, all other things equal, shorter sequences will become more likely to bind together in relation to longer sequences.

In one example, at a first reaction rate, two five-base sequences may be 10% more likely to bind together than would two seven-base sequences that may represent a different data element.

But if the reaction rate is increased, for example, by manipulating a physical property of a medium in which the reaction occurs, the relative rate of bonding of shorter strands of nucleobases may increase proportionally faster than does the rate of bonding of longer sequences. At a new, higher reaction rate, the five-base sequences may, for example become 25% more likely to bind than the seven-length sequences.

Such an effect may greatly affect an outcome of a DNA-computing operation. In the current example, if the nucleobase strands are mixed together and allowed to combine in a reaction that proceeds at the lower first reaction rate, 52% of the resulting DNA molecules might be formed from five-base sequences and 48% may comprise seven-base sequences. This result might then be interpreted as indicating a data distribution that is 52% likely to have a characteristic or value associated with information encoded into the five-length sequences, and 48% likely to have a characteristic or value associated with data encoded into the seven-length sequences.

But if this same operation were performed at the second, higher, reaction rate, the relatively greater increase in the likelihood of smaller sequences combining might shift the results from a 52%/48% distribution to 56%/44%.

Embodiments of the present invention may use this principle in certain types of optimization, regression, artificial-intelligence, and regularization problems, or in other types of analyses, computations, and statistical methods, to best fit a function to a dataset or to optimize a data distribution or other type of results.

When performing a simple or multivariate linear-regression analysis, for example, useful results may be possible only if it is possible to identify acceptable ranges of an array of beta regression coefficients. If, therefore, such a linear regression is implemented as a machine-language algorithm on a DNA-computing platform, the resulting distribution of molecular-DNA results may produce a reliable result only if the DNA-computing operation can be programmed to comprise an optimal range of scalar or vector beta values.

Embodiments of this invention may be used to identify such optimal values of a metafactor, weighting, coefficient, offset, constant multiplier, or other biasing factor by identifying an optimal reaction rate and adjusting physical characteristics of the reaction to ensure that the reaction takes place at that optimal rate.

Furthermore, in a machine-learning application on a DNA-computing platform, such an adjustment may represent a global revision of a knowledge base, inference engine, or other model represented by very large numbers of DNA molecules. In this way, by configuring both physical and chemical parameters of a DNA-computing operation, certain types of learned behavior may be then be represented and optimized by a simple adjustment to an environmental or physical parameter of the DNA reaction. In embodiments and examples described in this document, those parameters may comprise any combination of factors that affect kinetic properties of the DNA reaction.

FIG. 1 shows a structure of a computer system and computer program code that may be used to implement a method for using machine-learning methods to perform linear regression on a DNA-computing platform in accordance with embodiments of the present invention. FIG. 1 refers to objects 101-115.

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In FIG. 1, computer system 101 comprises a processor 103 coupled through one or more I/O Interfaces 109 to one or more hardware data storage devices 111 and one or more I/O devices 113 and 115.

Hardware data storage devices 111 may include, but are not limited to, magnetic tape drives, fixed or removable hard disks, optical discs, storage-equipped mobile devices, and solid-state random-access or read-only storage devices. I/O devices may comprise, but are not limited to: input devices 113, such as keyboards, scanners, handheld telecommunications devices, touch-sensitive displays, tablets, biometric readers, joysticks, trackballs, or computer mice; and output devices 115, which may comprise, but are not limited to printers, plotters, tablets, mobile telephones, displays, or sound-producing devices. Data storage devices 111, input devices 113, and output devices 115 may be located either locally or at remote sites from which they are connected to I/O Interface 109 through a network interface.

Processor 103 may also be connected to one or more memory devices 105, which may include, but are not limited to, Dynamic RAM (DRAM), Static RAM (SRAM), Programmable Read-Only Memory (PROM), Field-Programmable Gate Arrays (FPGA), Secure Digital memory cards, SIM cards, or other types of memory devices.

At least one memory device 105 contains stored computer program code 107, which is a computer program that comprises computer-executable instructions. The stored computer program code includes a program that implements a method for using machine-learning methods to perform linear regression on a DNA-computing platform in accordance with embodiments of the present invention, and may implement other embodiments described in this specification, including the methods illustrated in FIGS. 1-2. The data storage devices 111 may store the computer program code 107. Computer program code 107 stored in the storage devices 111 is configured to be executed by processor 103 via the memory devices 105. Processor 103 executes the stored computer program code 107.

Thus the present invention discloses a process for supporting computer infrastructure, integrating, hosting, maintaining, and deploying computer-readable code into the computer system 101, wherein the code in combination with the computer system 101 is capable of performing a method for using machine-learning methods to perform linear regression on a DNA-computing platform.

Any of the components of the present invention could be created, integrated, hosted, maintained, deployed, managed, serviced, supported, etc. by a service provider who offers to facilitate a method for using machine-learning methods to perform linear regression on a DNA-computing platform. Thus the present invention discloses a process for deploying or integrating computing infrastructure, comprising integrating computer-readable code into the computer system 101, wherein the code in combination with the computer system 101 is capable of performing a method for using machine-learning methods to perform linear regression on a DNA-computing platform.

One or more data storage units 111 (or one or more additional memory devices not shown in FIG. 1) may be used as a computer-readable hardware storage device having a computer-readable program embodied therein and/or having other data stored therein, wherein the computer-readable program comprises stored computer program code 107. Generally, a computer program product (or, alternatively, an article of manufacture) of computer system 101 may comprise said computer-readable hardware storage device.

While it is understood that program code 107 for using machine-learning methods to perform linear regression on a DNA-computing platform may be deployed by manually loading the program code 107 directly into client, server, and proxy computers (not shown) by loading the program code 107 into a computer-readable storage medium (e.g., computer data storage device 111), program code 107 may also be automatically or semi-automatically deployed into computer system 101 by sending program code 107 to a central server (e.g., computer system 101) or to a group of central servers. Program code 107 may then be downloaded into client computers (not shown) that will execute program code 107.

Alternatively, program code 107 may be sent directly to the client computer via e-mail. Program code 107 may then either be detached to a directory on the client computer or loaded into a directory on the client computer by an e-mail option that selects a program that detaches program code 107 into the directory.

Another alternative is to send program code 107 directly to a directory on the client computer hard drive. If proxy servers are configured, the process selects the proxy server code, determines on which computers to place the proxy servers' code, transmits the proxy server code, and then installs the proxy server code on the proxy computer. Program code 107 is then transmitted to the proxy server and stored on the proxy server.

In one embodiment, program code 107 for using machine-learning methods to perform linear regression on a DNA-computing platform is integrated into a client, server and network environment by providing for program code 107 to coexist with software applications (not shown), operating systems (not shown) and network operating systems software (not shown) and then installing program code 107 on the clients and servers in the environment where program code 107 will function.

The first step of the aforementioned integration of code included in program code 107 is to identify any software on the clients and servers, including the network operating system (not shown), where program code 107 will be deployed that are required by program code 107 or that work in conjunction with program code 107. This identified software includes the network operating system, where the network operating system comprises software that enhances a basic operating system by adding networking features. Next, the software applications and version numbers are identified and compared to a list of software applications and correct version numbers that have been tested to work with program code 107. A software application that is missing or that does not match a correct version number is upgraded to the correct version.

A program instruction that passes parameters from program code 107 to a software application is checked to ensure that the instruction's parameter list matches a parameter list required by the program code 107. Conversely, a parameter passed by the software application to program code 107 is checked to ensure that the parameter matches a parameter required by program code 107. The client and server operating systems, including the network operating systems, are identified and compared to a list of operating systems, version numbers, and network software programs that have been tested to work with program code 107. An operating system, version number, or network software program that does not match an entry of the list of tested operating systems and version numbers is upgraded to the listed level on the client computers and upgraded to the listed level on the server computers.

After ensuring that the software, where program code 107 is to be deployed, is at a correct version level that has been tested to work with program code 107, the integration is completed by installing program code 107 on the clients and servers.

Embodiments of the present invention may be implemented as a method performed by a processor of a computer system, as a computer program product, as a computer system, or as a processor-performed process or service for supporting computer infrastructure.

Figure 2:
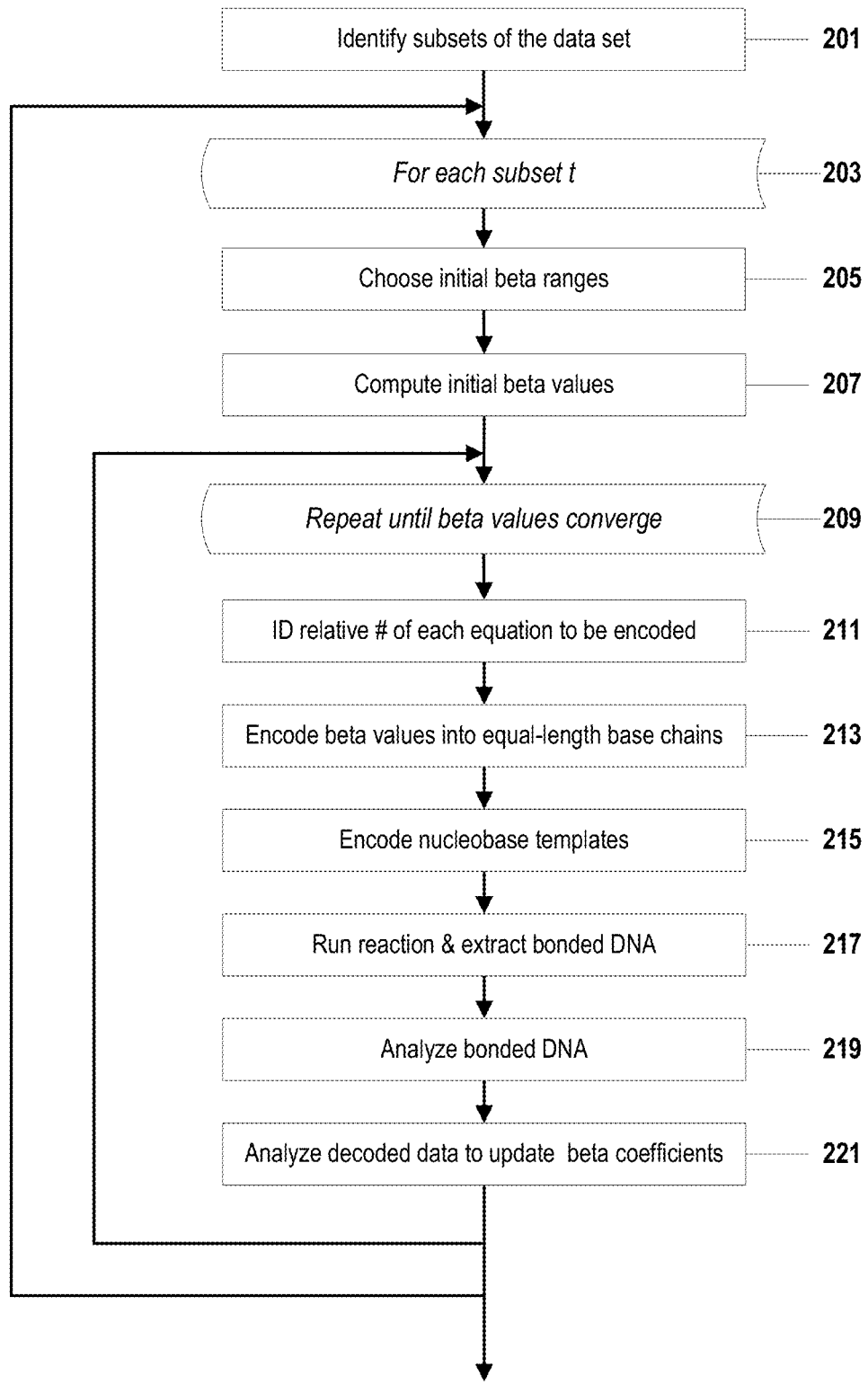
FIG. 2 is a flow chart that illustrates a method for using a machine-learning method to perform linear regression on a DNA-computing platform.

FIG. 2 is a flow chart that illustrates a method for using a machine-learning algorithm to perform a linear-regression analysis on a DNA-computing platform in accordance with embodiments of the present invention. FIG. 2 comprises steps 201-221. The methods, embodiments, and examples associated with this figure illustrate a method for performing such analyses by optimizing values of an array of "beta" regression coefficients of a system of linear equations.

Linear regression is a mathematical procedure for modeling, or determining coefficients of, a function Y that defines a relationship between a dependent variable (y) and one or more independent variables $x_i$. In the examples of FIG. 2, one or more processors of a computer system use machine-learning methodologies to perform a regression analysis upon a linear function of the form Y(x). But this should not be construed to limit embodiments of the present invention to such simple regressions, to linear-regression analyses in general, or to other types of computations that may be suited to implementation via a machine-learning algorithm.

A linear regression analysis performed on an input data set of (x,y) values may, for example, identify a trend line $Y(x_t)$ that defines a linear relationship between a dependent variable x and an independent variable y over a span of time t. Such a trend line may be useful in fields like financial analysis, where it might, for example, predict behavior of a stock price by inferring a straight-line or smooth curve function from a set of scattered stock prices recorded during time t.

Machine-learning algorithms may be especially well-suited to implementing linear-regression analyses. Such algorithms may perform an iterative data-fitting procedure upon an input data set that with each iteration teaches itself to more accurately identify a relationship between independent and dependent variables of the data set. This self-learning function may be used to identify a better-fitting model with each iteration until a sufficiently accurate fit is obtained.

As mentioned above, obtaining a useful result from a linear-regression analysis may comprise identifying optimal values of an array of "beta" regression coefficients $\beta_i$ that are each associated with an independent scalar variable x or with an element of an array of independent variables $x_i$.

In a system of linear equations, a first beta coefficient may set a Y-axis intercept point for a linear function Y, and each other beta coefficient weights a relationship between a dependent variable y and one dependent variable $x_i$. A proper selection of beta values may, therefore, identify nearly all essential characteristics of a linear function Y and choosing optimal beta values for each range of a data set is thus an important component of an efficient, accurate linear regression.

In step 201, one or more processors of a computer system, using means known to those skilled in the art of statistical analysis, divide an input data set into contiguous segments bounded by a set of knots. This allows the linear regression analysis to be performed on smaller, contiguous subsets of data that may be at least partially free of discontinuities that hamper efforts to efficiently and accurate fit a data set to a linear function. When the regression is implemented in later steps on a DNA-computing platform, performing the regression on properly chosen subsets of the original data set may eliminate a need for unnecessary extra iterations or may increase a likelihood of a smooth, accurate, noise-free model of linear function Y.

As is known in the art, a knot may be a critical point, inflection point, or discontinuity in a data set. In some analyses, a data set may be stratified or organized into subsets delineated by the knots. In other cases, a first-order estimate of a curve defined by fitting a function Y to a data set may be formed by fitting a spline to each data segment bounded by a pair of consecutive knots. In yet other cases, a data set may simply be arbitrarily divided into equally spaced segments, which may optionally be weighted by a dataset-density function.

Regardless of how the knots or data segments are chosen, better regression results may be obtained if the number, size, and boundaries of each segment are at least partially determined by how smooth or how accurate a fit is desired. As is known in the art, a greater number of knots, resulting in a larger number of smaller segments, may increase a total number of regression analyses that must be performed, since a separate analysis may be performed on each segment. The extra overhead incurred by this greater number of analyses, may, however, be offset by a reduced number of iterations per regression, or a reduced computational overhead imposed by each regression. Identifying an optimal set of data segments may thus be a tradeoff dictated at least in part by characteristics of a particular data set, that is best selected by a person skilled in the field of statistical analysis.

Step 203 initiates an iterative procedure of steps 203-221, which is performed once upon each subset of x values comprised by a knot-bounded segment. If, for example, a data set was partitioned in step 201 into ten subsets by eleven knots, the procedure of steps 203-221 would be performed ten times, or once upon each of the ten subsets.

When describing each iteration of the procedure of steps 203-221 this document will refer to the data subset being regressed by the current iteration as comprising data points collected over a range of time (or of a mathematically equivalent parameter) t. Variable $\bar{x}_t$, for example, would refer to an arithmetic mean of variable x over time span t.

In step 205, the one or more processors select initial ranges of values of an array of beta coefficients of the function Y to be regressed. These initial beta ranges may be estimated by mathematical methods known to those skilled in the art, such as transfer learning. Such a range may, for example, have been determined or transferred from prior experimental data, or may be chosen as a function of a range associated with previously published analyses performed upon similar data. In some embodiments, a range of possible values for a beta coefficient may be identified by an educated guess based on expert knowledge possessed by experienced statisticians skilled in the art of linear regression, or by arbitrarily choosing a pair of boundary points that are each equidistant from a center point.

Because these initial beta ranges merely seed an iterative self-learning procedure, it is not essential to initially select ideal values. A better guess may result in a more efficient performance of the method of FIG. 2, but the method, through its self-learning characteristics, will eventually self-correct even an imperfect initial choice.

In step 207, the one or more processors use a novel combination of steps to select a set of initial candidate values for each beta coefficient in the function being regressed.

In one example, a method of the present invention might be used to fit data points to a function Y that returns an expected number of points scored in a fantasy football game as a function of a total number of running attempts and a total number of passing attempts during that game.

Here, a linear regression analysis might be used to predict a function Y defined by equation:

$$E(Y|\bar{x}_t) = \beta_0 + \beta_1 x_1 + \beta_2 x_2$$

In this equation, $E(Y|\bar{x}_t)$ is an expected value of $Y(\bar{x}_t)$, where $\bar{x}_t$ is an arithmetic mean of a subset of values of independent variable x identified by input data points within a subset t of the input data set, where subset t was identified in step 201 as comprising data points sampled over a range of time t, and is being processed by the current iteration of the procedure of steps 203-221. In our current example, there are two independent variables: $x_1$ is a total number of passing attempts in a game and $x_2$ is a total number of running attempts.

Given that Y is defined to be a function of the general form $Y(\bar{x}_t) = \beta_0 + \beta_1 x_1 + \beta_2 x_2$, a linear regression analysis may fully define expected values of Y within a subset range t of the input data set by determining values for the three beta coefficients $\beta_0$, $\beta_1$, and $\beta_2$ within range t, where $\beta_0$ is a constant that may adjust the y-intercept point of function Y, $\beta_1$ is a coefficient multiplier of $x_1$, and $\beta_2$ is a coefficient multiplier of $x_2$. Embodiments of the present invention use the method described above (and further illustrated below) use methods of DNA computing to select initial beta values.

Using a machine-learning approach to identifying optimal beta values begins by seeding a model of function Y with initial values. A broad range of beta values may be selected, but beta-optimization may be made more efficient by using mathematical conventions and techniques known in the art to select initial values that will minimize a number of iterations of steps of FIG. 2 that will be needed to identify best values.

In the current example, using methods known to those skilled in the art, we might, for example, initialize each of the three beta coefficients to an average value of all other beta values already known to have optimized similar point-predicting functions for other teams in the same football league.

Another known method might be to set each beta coefficient to a random value rand( ) in a range [a,c] that is then normalized to fall between values d and e.

Values of a, b, d, and e, might be selected as a function of a range of a randomization function rand( ) used to generate random values, or by a learning step size of the machine-learning procedure, which may be selected by a person skilled in the art as a mean of optimizing performance.

In this latter case, for example, initial beta values might be chosen by the following equations:

$$\beta_0 = 1 + \frac{(rand() - d) * (c - \alpha)}{(e - d)}$$

$$\beta_1 = 1 + \frac{(rand() - d) * (c - \alpha)}{(e - d)}$$

$$\beta_2 = 1 + \frac{(rand() - d) * (c - \alpha)}{(e - d)}$$

In one example, random selections might produce initial beta values of:

$\beta_1 = 36$, $\beta_1 = 15$, and $\beta_2 = 33$

We next define a sliding window that arbitrarily defines a range of values centered around each beta. The size of the window, which identifies a number of values in a range, might be selected as a function of expert knowledge of a person skilled in the art, or could be determined as a function of the aforementioned learning step size of the machine-learning procedure.

In this example, we select a range of ±6 for $\beta_0$, ±3 for $\beta_1$, and ±5 for $\beta_2$, resulting in ranges bounded by the beta pairs:

$\beta_1$: $\beta_{01} = 30$, $\beta_{02} = 42$, $\beta_1$: $\beta_{11} = 12$, $\beta_{12} = 18$, and $\beta_2$: $\beta_{21} = 28$, $\beta_{22} = 38$.

An accuracy of a regression analysis based on these bounded ranges may be computed for each beta value, in combination with $\beta_0$, by using a known residual sum of squared errors computation, as mentioned above.

In this example, such a method would result in the equations:

$$E(Y|\bar{x}_t) = \beta_{01} + \beta_{11} x_1 \quad (1)$$

$$E(Y|\bar{x}_t) = \beta_{02} + \beta_{11} x_1 \quad (2)$$

$$E(Y|\bar{x}_t) = \beta_{01} + \beta_{12} x_1 \quad (3)$$

$$E(Y|\bar{x}_t) = \beta_{02} + \beta_{12} x_1 \quad (4)$$

$$E(Y|\bar{x}_t) = \beta_{01} + \beta_{21} x_1 \quad (5)$$

$$E(Y|\bar{x}_t) = \beta_{02} + \beta_{21} x_1 \quad (6)$$

$$E(Y|\bar{x}_t) = \beta_{01} + \beta_{22} x_1 \quad (7)$$

$$E(Y|\bar{x}_t) = \beta_{02} + \beta_{22} x_1 \quad (8)$$

Plugging the exemplary values into these equations yields:

$$E(Y|\bar{x}_t) = 30 + 12 x_1 \quad (1)$$

$$E(Y|\bar{x}_t) = 42 + 12 x_1 \quad (2)$$

$$E(Y|\bar{x}_t) = 30 + 18 x_1 \quad (3)$$

$$E(Y|\bar{x}_t) = 42 + 18 x_1 \quad (4)$$

$$E(Y|\bar{x}_t) = 30 + 28 x_2 \quad (5)$$

$$E(Y|\bar{x}_t) = 42 + 28 x_2 \quad (6)$$

$$E(Y|\bar{x}_t) = 30 + 38 x_2 \quad (7)$$

$$E(Y|\bar{x}_t) = 42 + 38 x_2 \quad (8)$$

Step 209 begins an inner-nested iterative procedure of steps 209-221. Each iteration of this procedure performs steps related to encoding the system of linear equations derived in steps 201-207 into nucleobase chains, performing a DNA-computing operation upon those chains, decoding data from the DNA molecules that result from that operation, and using that data to further optimize beta-coefficient values of the system of equations. If those values have not converged at the conclusion of an iteration of steps 209-221, another iteration begins, this time starting with the updated beta values obtained by the previous iteration.

In step 211, the one or more processors determine relative numbers of copies of each equation to encode into nucleobase chains. In a real-world DNA-computing operation, a particular encoded data element or equation may be encoded into thousands of copies of a chain of nucleobases and embodiments of the present invention choose relative numbers of copies of each equation as a function of beta weightings needed to optimize the linear regression represented by the DNA-computing operation.

The one or more processors determine these relative numbers by first identifying a residual sum of squares (RSS) error rate for each of equation (1)-(8), using computational procedures known to those skilled in the art. In some embodiments, initial values of these error rates may be estimated by using a conventional computer platform to run one or more preliminary test regressions on the data set to be regressed.

In such embodiments, the processor may compute each equation's error rate by means of the known residual sum-of-squares equation:

$$\text{Error rate} = \sum_{k=0}^{N} (E(Y|\bar{x}_t)_k - y_k)^2$$

where N=the total number of data points in data segment t and y is a target value of a data point k comprised by data segment t. This target value may be predicted by function Y (which, in the first iteration of the procedure of steps 209-221, may itself have been estimated from experimental values). In our ongoing example, each performance of this equation yields a numeric error rate for one of the eight equations.

The one or more processors then performs a series of computations that translates each of the computed error rates into a percent value, such that a sum of all the error rates yields a value of 100%.

In one example, the residual sum-of-squares equation may have produced eight error rates e[1] . . . e[8], where e[1] has the greatest amplitude of the eight error rates. The processors divide each of e[1] . . . e[8] by the magnitude of e[1] to ensure that all eight error rates fall into a range between of 0 and 1, inclusively.

The processors then subtract each normalized error from a value of one and divide each of those differences by a sum of all eight differences. This procedure scales each of the eight differences such that they add up to a total value of one. As described above, in our example, the eight computed error rates may thus respectively be represented as eight percent values that sum to a value of 100%.

The resulting normalized, relative error rates determine relative proportions in which each the data comprised by each equation (1)-(8) will be encoded into chains of nucleobases that will serve as input for a DNA-computing operation that will perform the linear-regression.

If, for example, a normalized, relative error rate of equation (1) is 20%, then equation (1) will be encoded in step 213 into a number of nucleobase chains that is 20% of the total number of nucleobase chains into which any of the eight equations have been encoded.

In step 213, the system of linear equations derived in the previous steps are each encoded into chains of nucleobases. This encoding may be performed by any means known in the art, but embodiments of the present invention described here encode the beta values identified by each equation into nucleobase strands by first converting the latest values of each equation's beta coefficients into base 3 values that may be represented by three of the four DNA nucleobases, allowing the fourth nucleobase to be used as a filler. As described above, instances of the filler nucleobase may be added to the end of any chain in order to ensure that all chains are of the same length (that is, to ensure that each chain contains a same number of bases).

In the nomenclature convention used in this document, each beta value may be encoded into three base-3 representations comprised of digits 0, 1, and 2. Here, we arbitrarily associate these digits respectively with bases A1, A2, and B1, each uniquely representing a distinct, unique base, and where A1 and A2 represent first pair of complementary nucleobases that readily bind into a base pair. A fourth distinct nucleobase B2 is selected as a filler value, where B2 and B1 represent a second pair of complementary nucleobases that bind into a base pair.

In our running example, four nucleobases identified by our document-specific naming convention as A1, A2, B1, and B2 may be arbitrarily chosen to respectively encode into base-3 digits 0, 2, and 1, and to a filler value that does not correspond to an information-bearing base-3 digit. Such a representation might then encode base-3 value 2013 as a three-base chain A2-A1-B1 and encode base-3 value 001123 as A1-A1-B1-B1-A2.

In such an example, the previously derived beta values of equation (1) would be translated into base-3 representations that are then encoded into information-bearing chromosome as:

$$E(Y|\bar{x}_t) = 30 + 12x_1$$

$$E(Y|\bar{x}_t) = 1010_3 + 110_3 x_1$$

$$E(Y|\bar{x}_t) = B1\text{-}A1\text{-}B1\text{-}A1 + B1\text{-}B1\text{-}A1 \quad (1)$$

The processor then encodes each of the other equations (2)-(8) in the same way and then sets them to a same standard length by delimiting the two base-3 values represented by the encoded equation with a variable number of filler bases. In this way, all eight equations are encoded to strands of nucleobases of the same length.

This standard length may be selected by any means known to the art, such as setting it to the shortest length capable of facilitating a DNA-forming chemical reaction, but must be set to a length sufficient to store the longest encoded data values.

In our example, if nucleobase B2 has been chosen as a filler, and if a chain length of 15 is selected, the encoded data of equation (1) might be stored in a nucleobase strand as:

$$E(Y|\bar{x}_t) = B1\text{-}A1\text{-}B1\text{-}A1 + B1\text{-}B1\text{-}A1 \rightarrow B1\text{-}A1\text{-}B1\text{-}A1\text{-}B2\text{-}B2\text{-}B2\text{-}B2\text{-}B2\text{-}B2\text{-}B2\text{-}B2\text{-}B1\text{-}B1\text{-}A1$$

At the conclusion of this encoding process, the one or more processors may direct the physical creation of nucleobase chains that incorporate the specific information-bearing base sequences determined by the above procedure. This creation of actual base chains may be performed by any method known in the art.

As mentioned above, each equation is encoded into a distinct chain of nucleobases, and large numbers of copies of each such distinct chain may be created. The absolute number of copies is not an essential element of this invention, but the relative numbers of copies of each equation is determined by the relative error rates associated with each equation in step 211.

In step 215, the one or more processors design and direct the creation of a set of corresponding templates, implemented as strands of nucleobases. Each of these template strands should be capable of binding to one of the aforementioned equation-encoded strands generated in step 213. Once bound by means of a Watson Crick reaction known in the art, each equation/template pair of strands will form a double-helix DNA molecule. The number of different types of templates produced equal the number of equation DNA strands, such that every equation-encoded strand of bases may bond to a complementary, matching template strand. If, as in our running example, a system of eight linear equations was encoded into nucleobase chains in step 213, eight distinct, matching templates will be created by similar methods.

Although the relative proportions of each type of template strand are equal to the relative proportions of each type of equation-data strand, most embodiments will comprise far greater total numbers of template strands than of equation-data strands. In our example, 1000 copies of each template will be created for each copy of that template's corresponding equation-data strand. Such large ratios may facilitate the highly parallel action of a DNA-computing operation, and help ensure that enough strands bond to ensure statistically relevant results.

In our ongoing example, a first template may be configured to complement a base chain that has encoded the beta coefficients of equation (1).

$$E(Y|(\bar{x}_t) = B1\text{-}A1\text{-}B1\text{-}A1\text{-}B2\text{-}B2\text{-}B2\text{-}B2\text{-}B2\text{-}B2\text{-}B2\text{-}B2\text{-}B1\text{-}B1\text{-}A1 \quad (1)$$

That first template may thus comprise the complementary chain:

$$E(Y|(\bar{x}_t)_{template} = B2\text{-}A2\text{-}B2\text{-}A2\text{-}B1\text{-}B1\text{-}B1\text{-}B1\text{-}B1\text{-}B1\text{-}B1\text{-}B1\text{-}B2\text{-}B2\text{-}A2$$

In step 217, the equation and template nucleobase strands created above are mixed together in a medium known to those skilled in the art, such as water or ammonia solution. The strands are allowed to bind together in a DNA-computing operation for a fixed duration of time according to methods and techniques known to those skilled in the art. In such a reaction, each pair of strands will most likely bind when they contain complementary patterns of nucleobases. As mentioned earlier, and as is known in the art, a pair of nucleobase chains are likely to bond together when the bonding will result in a sequence of at least three base pairs.

In one example, a data-encoded strand that contains a base sequence

B1-A1-B1-A1-B2-B2 might more readily bind with a sequence B1-A1-B1 would readily form three base pairs with the template strand's B2-A2-B2 template strand that contains a base sequence

B2-A2-B2-A1-B1-B1-B1 because the data strand's sequence.

However, a data-encoded strand

A1-A1-A1-A1-B2 might not bind with a template strand

B2-A2-B2-A1-B1-B1-B1 because no sequence of three or more nucleobases in the template strand form a pattern that is complementary to a sequence of bases of the data strand.

At the conclusion of the prescribed duration of time, the reaction is chemically neutralized and the resulting DNA molecules extracted and analyzed, using techniques known to those skilled in arts related to molecular biology or chemistry.

Several factors may affect the outcome of this DNA-computing operation. The results of this reaction, for example, may be affected by adjusting a physical characteristic of the reaction or of the environment in which the reaction occurs, such as a temperature or a hydrostatic pressure, or by introducing a catalyst into the medium in which the reaction occurs.

In such cases, if a value of such a characteristic alters a reaction rate of the reaction, such an alteration may change a likelihood that certain strands will bind together. In particular, a likelihood that longer strands will combine increases more quickly as a function of a reaction rate than does a likelihood that shorter strands will combine.

At the conclusion of the reaction, the resulting DNA molecules are filtered by means known in the art, retaining only those molecules created from a pairing of a template strand and a strand into which was encoded one of the beta equations. This filtering may be done by any means known in the art, such as centrifuging the results and selecting only those molecules that comprise a distinctive marker pattern that identifies a desired molecule.

In step 219, the one or more processors direct that the genetic material retrieved in step 217 is analyzed or otherwise processed. This analyzing or otherwise processing may comprise a decoding procedure that is complementary to the encoding or translation procedures used to encode equation and template data into the base strands that were mixed together to initiate the DNA-computing operation.

In embodiments of the present invention, the one or more processors in this step employ this decoding to determine how many of the bonded DNA molecules were formed from base sequences that represented each of equations (1)-(8). These relative numbers will be used in step 221 to "teach" the machine-language algorithm how to adjust beta coefficients $\beta_0$, $\beta_1$, and $\beta_2$ to more accurately model function Y over segment t.

In the current example, this determining may reveal that the bonded DNA comprises DNA molecules formed from base strings representing beta coefficients of equations (1)-(8) in the following proportions:
(1) 30%
(2) 20%
(3) 10%
(4) 20%
(5) 8%
(6) 3%
(7) 6%
(8) 3%

In other words, 30% of the bonded DNA was formed when a nucleobase strand into which had been encoded the beta coefficient values of equation (1) bonded with its complementary nucleobase template; 20% of the bonded DNA was formed from a strand that encoded the coefficients of equation (2); and so forth.

In step 221, the one or more processor use the DNA proportions identified in step 219 to generate weightings, and then use these weightings to adjust beta coefficients $\beta_0$, $\beta_1$, and $\beta_2$ to more accurately model function Y over segment t. If these adjusted coefficients are not deemed to be a final, optimized value, another iteration of the iterative procedure of steps 209-221 begins, substituting these adjusted beta values for the previous values identified at the beginning of the previous iteration. Repeating each iteration with updated equations produced in the way by the previous iteration allows the continuously varying system of equations to act as a self-learning, continuously optimizing, model of function Y.

In our ongoing example, equations (1)-(8) are of the form:

$$E(Y|\bar{x}_t) = \beta_{01} + \beta_{11} x_1 \quad (1)$$

$$E(Y|\bar{x}_t) = \beta_{02} + \beta_{11} x_1 \quad (2)$$

$$E(Y|\bar{x}_t) = \beta_{01} + \beta_{12} x_1 \quad (3)$$

$$E(Y|\bar{x}_t) = \beta_{02} + \beta_{12} x_1 \quad (4)$$

$$E(Y|\bar{x}_t) = \beta_{01} + \beta_{21} x_1 \quad (5)$$

$$E(Y|\bar{x}_t) = \beta_{02} + \beta_{21} x_1 \quad (6)$$

$$E(Y|\bar{x}_t) = \beta_{01} + \beta_{22} x_1 \quad (7)$$

$$E(Y|\bar{x}_t) = \beta_{02} + \beta_{22} x_1 \quad (8)$$

Here, equations (1)-(4) comprise coefficients $\beta_{11}$ and $\beta_{12}$, which respectively identify lower and upper boundaries of a range of values of beta coefficient $\beta_1$. Embodiments of the present invention will thus adjust the value of $\beta_1$ to a new revised value $\beta'_1$ as a function of the relative numbers of equations (1)-(4) to successfully bond in step 217.

Similarly, equations (5)-(8) comprise coefficients $\beta_{21}$ and $\beta_{22}$, which respectively identify lower and upper boundaries of a range of values of beta coefficient $\beta_2$. Embodiments of the present invention will thus adjust the value of $\beta_2$ to a new revised value $\beta'_2$ as a function of the relative numbers of equations (5)-(8) to successfully bond in step 217.

Equations (1)-(8) all comprise coefficients $\beta_{01}$ or $\beta_{02}$, which respectively identify lower and upper boundaries of a range of values of beta coefficient $\beta_0$. Embodiments of the present invention will thus adjust the value of $\beta_0$ to a new revised value $\beta'_0$ as a function of the relative numbers of equations (1)-(8) to successfully bond in step 217.

Although the beta coefficients themselves are fine-tuned by each iteration of the procedure of steps 209-221, the initial sizes of the ranges of coefficients selected in step 205, which falls outside of this iterative procedure, do not change with each iteration. In our ongoing example, therefore, the ranges of values that may be assigned to each of the beta coefficients remains: $\pm 6$ for $\beta_0$, $\pm 3$ for $\beta_1$, and $\pm 5$ for $\beta_2$.

In our ongoing example, the one or more processors first derives "sum-weighted" probabilities for each beta coefficient (indicated by an "sw" subscript). Each of these sum-weighted values of a coefficient is a simple sum of probabilities of each equation that comprises that coefficient.

$$\beta_{0sw} = (0.3 + 0.2 + 0.1 + 0.2 + 0.08 + 0.03 + 0.06 + 0.03)$$

$$\beta_{1sw} = (0.3 + 0.2 + 0.1 + 0.2)$$

$$\beta_{2sw} = (0.08 + 0.03 + 0.06 + 0.03)$$

The one or more processors then identifies adjusted values of the beta coefficients (identified respectively as $\beta'_0$, $\beta'_1$, and $\beta'_2$ $$\beta'_0 = \frac{0.3}{\beta_{0sw}}\beta'_{01} + \frac{0.2}{\beta_{0sw}}\beta'_{02} + \frac{0.1}{\beta_{0sw}} + \beta'_{01} + \frac{0.2}{\beta_{0sw}}\beta'_{02} + \frac{0.08}{\beta_{0sw}}\beta'_{01} + \frac{0.03}{\beta_{0sw}}\beta'_{02} + \frac{0.06}{\beta_{0sw}}\beta'_{01} + \frac{0.03}{\beta_{0sw}}$$

$$\beta'_1 = \frac{0.3}{\beta_{1sw}}\beta'_{11} + \frac{0.2}{\beta_{1sw}}\beta'_{12} + \frac{0.1}{\beta_{1sw}} + \beta'_{11} + \frac{0.2}{\beta_{1sw}}\beta'_{12}$$

$$\beta'_2 = \frac{0.08}{\beta_{2sw}}\beta'_{21} + \frac{0.03}{\beta_{2sw}}\beta'_{22} + \frac{0.06}{\beta_{2sw}}\beta'_{21} + \frac{0.03}{\beta_{2sw}}\beta'_{22}$$

Here, $\beta'_{01}$, $\beta'_{02}$, $\beta'_{11}$, $\beta'_{12}$, $\beta'_{21}$, and $\beta'_{22}$ are selected by a method analogous to that by which the values of $\beta_{01}$, $\beta_{02}$, $\beta_{11}$, $\beta_{12}$, and $\beta_{22}$ were selected in step 207, as respective lower ad upper boundaries of ranges of possible beta values, where the size of each range remains the same as it was in step 207, but the centers of each range are now identified by adjusted values as $\beta'_0$, $\beta'_1$, and $\beta'_2$.

That is, in our ongoing example, all variables may be expressed in terms of constants, of experimentally derived values identified by means of DNA-computing step 217, and of values of three variables $\beta'_0$, $\beta'_1$, and $\beta'_2$:

$$\beta'_{01} = \beta'_0 + 6$$

$$\beta'_{02} = \beta'_0 - 6$$

$$\beta'_{11} = \beta'_1 + 3$$

$$\beta'_{12} = \beta'_1 - 3$$

$\beta'_{21} = \beta'_2 + 5$ $\beta'_{22} = \beta'_2 - 5$

In other embodiments that comprise different numbers of equations or different numbers of beta coefficients, similar procedures may be employed to produce analogous weightings. In all cases, however, if another iteration of the iterative procedure of steps 209-221 is performed, the resulting adjusted beta coefficients, expressed in this manner, are substituted for the original beta coefficients at the outset of that iteration, and the iteration is repeated in order to derive more accurate coefficient values, and to thus use the weightings learned in the previous iteration from the DNA-computing operation to more accurately predict function Y.

The one or more processors repeat the iterative procedure of steps 209-221 in this manner until a threshold condition is detected at the conclusion of an iteration that indicates a likelihood that the most recently adjusted values of the beta coefficients have sufficiently converged to an optimal value. This threshold condition might, for example, be satisfied when differences between two or more successively updated values fall below a threshold level, when nucleobase strands encoding each equation's coefficients bind successfully in step 217 in proportions that fall below a threshold value, or when nucleobase strands encoding one particular equation's coefficients bind successfully in step 217 in proportions that fall above a threshold value. Other implementation-dependent methods of identifying convergence are possible, and are known in the art.

When such a convergence condition is satisfied, the method of FIG. 2 is deemed to be complete and the embodiment concludes.

What is claimed is:

1. A method for using machine-learning on a DNA-computing platform to perform linear regression, the method comprising:

a processor of a computer system identifying a first set of equal-length nucleobase sequences,
      wherein the identifying each sequence comprises selecting an order of nucleobases that each encode two or more numeric values of a set of numeric values, and
      wherein each value encoded into a first sequence of the first set of sequences represents an estimated value of a beta coefficient comprised by a corresponding first equation of a system of linear equations;

the processor further identifying a second set of equal-length nucleobase sequences that are each capable of bonding through a Watson Crick reaction to a corresponding sequence of the first set of equal-length nucleobase sequences;

the processor adjusting each value of the set of numeric values as a function of a result of a Watson Crick reaction between a first set of nucleobase chains and a second set of nucleobase chains,
      wherein each chain of the first set of nucleobase chains comprises nucleobases ordered in a sequence of the first set of nucleobase sequences, and
      wherein each chain of the second set of nucleobase chains comprises nucleobases ordered in a sequence of the second set of nucleobase sequences;

the processor replacing each value of the set of numeric values with its corresponding adjusted value; and the processor repeating the identifying, further identifying, adjusting, and replacing until the adjusted values converge over two or more successive adjustings to a constant set of values.

2. The method of claim 1, further comprising:
   the processor encoding each value of the first sequence of the first set of sequences, wherein the encoding comprises:
      the processor translating each value of a beta coefficient comprised by the first equation into a base-3 numeral of a set of base-3 numerals;
      the processor representing each base-3 numeral of the of set of base-3 numerals as an analogous sequence of nucleobases, wherein each 0, 1, and 2 digit of the each base-3 numeral is uniquely represented as a nucleobase selected from a group comprising adenine, cytosine, guanine, and taurine;
      the processor identifying the first sequence of the first set of sequences as comprising analogous sequences of nucleobases that together represent base-3 values of all beta coefficients comprised by the first equation;
      the processor selecting a filler nucleobase from a group comprising adenine, cytosine, guanine, and taurine, wherein the filler nucleobase has not been used to represent a 0, 1, or 2 digit of any base-3 numeral of the set of base-3 numerals; and
      the processor setting the first sequence to the equal length by padding the first sequence, if necessary, with one or more instances of the filler nucleobase.

3. The method of claim 2,
   wherein each sequence of the first set of equal-length nucleobase sequences comprises base-3 encoded representations of all beta coefficients comprised by a corresponding equation of the system of linear equations, and
   wherein the equal length is the shortest length necessary to store a longest base-3 encoded representation of all beta coefficients comprised by an equation of the system of linear equations.

4. The method of claim 2, wherein the processor sets a template sequence of the second set of sequences to the equal length by padding the template sequence, if necessary, with one or more instances of a nucleobase that forms a base pair with the filler nucleobase.

5. The method of claim 1, further comprising:
   the processor computing a residual sum of squares error rate of a set of error rates for each set of beta coefficients of one equation of the system of linear equations;
   the processor normalizing the set of error rates such that a sum of all error rates of the set of error rates equals 100%; and
   the processor directing that the first set of nucleobase chains comprises multiple copies of each sequence of the first set of nucleobase sequences, wherein a relative number of copies of each sequence is a function of the set of error rates.

6. The method of claim 5, further comprising:
   the processor directing that a ratio between a sequence of the first set of nucleobase sequences and a corresponding template sequence of the second set of nucleobase sequences be at least 1000:1.

7. The method of claim 1, wherein the adjusting further comprises:
   the processor assigning a weighting to the beta coefficients of the first equation as a function of a number of DNA molecules formed by the Watson Crick reaction that comprise a nucleobase sequence that represents base-3 encoded values of beta coefficients of the first equation, relative to the total number of DNA molecules formed by the Watson Crick reaction.

8. The method of claim 1, further comprising providing at least one support service for at least one of creating, integrating, hosting, maintaining, and deploying computer-readable program code in the computer system, wherein the computer-readable program code in combination with the computer system is configured to implement the identifying, further identifying, adjusting, replacing, and repeating.

9. A computer program product, comprising a computer-readable hardware storage device having a computer-readable program code stored therein, said program code configured to be executed by a processor of a computer system to implement a method for using machine-learning on a DNA-computing platform to perform linear regression, the method comprising:
   the processor identifying a first set of equal-length nucleobase sequences,
      wherein the identifying each sequence comprises selecting an order of nucleobases that each encode two or more numeric values of a set of numeric values, and
      wherein each value encoded into a first sequence of the first set of sequences represents an estimated value of a beta coefficient comprised by a corresponding first equation of a system of linear equations;
   the processor further identifying a second set of equal-length nucleobase sequences that are each capable of bonding through a Watson Crick reaction to a corresponding sequence of the first set of equal-length nucleobase sequences;
   the processor adjusting each value of the set of numeric values as a function of a result of a Watson Crick reaction between a first set of nucleobase chains and a second set of nucleobase chains,
      wherein each chain of the first set of nucleobase chains comprises nucleobases ordered in a sequence of the first set of nucleobase sequences, and
      wherein each chain of the second set of nucleobase chains comprises nucleobases ordered in a sequence of the second set of nucleobase sequences;
   the processor replacing each value of the set of numeric values with its corresponding adjusted value; and
   the processor repeating the identifying, further identifying, adjusting, and replacing until the adjusted values converge over two or more successive adjustings to a constant set of values.

10. The computer program product of claim 9, further comprising:
   the processor encoding each value of the first sequence of the first set of sequences, wherein the encoding comprises:
      the processor translating each value of a beta coefficient comprised by the first equation into a base-3 numeral of a set of base-3 numerals;
      the processor representing each base-3 numeral of the of set of base-3 numerals as an analogous sequence of nucleobases, wherein each 0, 1, and 2 digit of the each base-3 numeral is uniquely represented as a nucleobase selected from a group comprising adenine, cytosine, guanine, and taurine;
      the processor identifying the first sequence of the first set of sequences as comprising analogous sequences of nucleobases that together represent base-3 values of all beta coefficients comprised by the first equation;
      the processor selecting a filler nucleobase from a group comprising adenine, cytosine, guanine, and taurine, wherein the filler nucleobase has not been used to represent a 0, 1, or 2 digit of any base-3 numeral of the set of base-3 numerals; and
      the processor setting the first sequence to the equal length by padding the first sequence, if necessary, with one or more instances of the filler nucleobase.

11. The computer program product of claim 10,
   wherein each sequence of the first set of equal-length nucleobase sequences comprises base-3 encoded representations of all beta coefficients comprised by a corresponding equation of the system of linear equations, and
   wherein the equal length is the shortest length necessary to store a longest base-3 encoded representation of all beta coefficients comprised by an equation of the system of linear equations.

12. The computer program product of claim 10, wherein the processor sets a template sequence of the second set of sequences to the equal length by padding the template sequence, if necessary, with one or more instances of a nucleobase that forms a base pair with the filler nucleobase.

13. The computer program product of claim 9, further comprising:
   the processor computing a residual sum of squares error rate of a set of error rates for each set of beta coefficients of one equation of the system of linear equations;
   the processor normalizing the set of error rates such that a sum of all error rates of the set of error rates equals 100%; and
   the processor directing that the first set of nucleobase chains comprises multiple copies of each sequence of the first set of nucleobase sequences, wherein a relative number of copies of each sequence is a function of the set of error rates.

14. The computer program product of claim 9, wherein the adjusting further comprises:
   the processor assigning a weighting to the beta coefficients of the first equation as a function of a number of DNA molecules formed by the Watson Crick reaction that comprise a nucleobase sequence that represents base-3 encoded values of beta coefficients of the first equation, relative to the total number of DNA molecules formed by the Watson Crick reaction.

15. A computer system comprising a processor, a memory coupled to said processor, and a computer-readable hardware storage device coupled to said processor, said storage device containing program code configured to be run by said processor via the memory to implement a method for using machine-learning on a DNA-computing platform to perform linear regression, the method comprising:
   the processor identifying a first set of equal-length nucleobase sequences,
      wherein the identifying each sequence comprises selecting an order of nucleobases that each encode two or more numeric values of a set of numeric values, and
      wherein each value encoded into a first sequence of the first set of sequences represents an estimated value of a beta coefficient comprised by a corresponding first equation of a system of linear equations;
   the processor further identifying a second set of equal-length nucleobase sequences that are each capable of bonding through a Watson Crick reaction to a corresponding sequence of the first set of equal-length nucleobase sequences;
   the processor adjusting each value of the set of numeric values as a function of a result of a Watson Crick reaction between a first set of nucleobase chains and a second set of nucleobase chains,
wherein each chain of the first set of nucleobase chains comprises nucleobases ordered in a sequence of the first set of nucleobase sequences, and
wherein each chain of the second set of nucleobase chains comprises nucleobases ordered in a sequence of the second set of nucleobase sequences;
the processor replacing each value of the set of numeric values with its corresponding adjusted value; and
the processor repeating the identifying, further identifying, adjusting, and replacing until the adjusted values converge over two or more successive adjustings to a constant set of values.

16. The computer system of claim 15, further comprising:
the processor encoding each value of the first sequence of the first set of sequences, wherein the encoding comprises:
the processor translating each value of a beta coefficient comprised by the first equation into a base-3 numeral of a set of base-3 numerals;
the processor representing each base-3 numeral of the of set of base-3 numerals as an analogous sequence of nucleobases, wherein each 0, 1, and 2 digit of the each base-3 numeral is uniquely represented as a nucleobase selected from a group comprising adenine, cytosine, guanine, and taurine;
the processor identifying the first sequence of the first set of sequences as comprising analogous sequences of nucleobases that together represent base-3 values of all beta coefficients comprised by the first equation;
the processor selecting a filler nucleobase from a group comprising adenine, cytosine, guanine, and taurine, wherein the filler nucleobase has not been used to represent a 0, 1, or 2 digit of any base-3 numeral of the set of base-3 numerals; and
the processor setting the first sequence to the equal length by padding the first sequence, if necessary, with one or more instances of the filler nucleobase.

17. The computer system of claim 16,
wherein each sequence of the first set of equal-length nucleobase sequences comprises base-3 encoded representations of all beta coefficients comprised by a corresponding equation of the system of linear equations, and
wherein the equal length is the shortest length necessary to store a longest base-3 encoded representation of all beta coefficients comprised by an equation of the system of linear equations.

18. The computer system of claim 16, wherein the processor sets a template sequence of the second set of sequences to the equal length by padding the template sequence, if necessary, with one or more instances of a nucleobase that forms a base pair with the filler nucleobase.

19. The computer system of claim 15, further comprising:
the processor computing a residual sum of squares error rate of a set of error rates for each set of beta coefficients of one equation of the system of linear equations;
the processor normalizing the set of error rates such that a sum of all error rates of the set of error rates equals 100%; and
the processor directing that the first set of nucleobase chains comprises multiple copies of each sequence of the first set of nucleobase sequences, wherein a relative number of copies of each sequence is a function of the set of error rates.

20. The computer system of claim 15, wherein the adjusting further comprises:
the processor assigning a weighting to the beta coefficients of the first equation as a function of a number of DNA molecules formed by the Watson Crick reaction that comprise a nucleobase sequence that represents base-3 encoded values of beta coefficients of the first equation, relative to the total number of DNA molecules formed by the Watson Crick reaction.

* * * * *